United States Patent [19]

Nedelec et al.

[11] 4,195,081
[45] Mar. 25, 1980

[54] TREATING PSYCHIC DISORDERS WITH TETRAHYDROPYRIDIN-4-YL-1H-INDOLES

[75] Inventors: Lucien Nedelec, Le Raincy; Jacques Guillaume, Sevran; Claude Dumont, Nogent-sur-Marne, all of France

[73] Assignee: Roussel Uclaf, Paris, France

[21] Appl. No.: 2,452

[22] Filed: Jan. 10, 1979

[30] Foreign Application Priority Data

Jan. 16, 1978 [FR] France .................. 78 01084

[51] Int. Cl.² .................................. A61K 31/44
[52] U.S. Cl. ..................................... 424/263
[58] Field of Search ..................... 424/274, 263

[56] References Cited
PUBLICATIONS

Chem. Abst., 83—131396v, (1975).

Primary Examiner—Stanley J. Friedman

Attorney, Agent, or Firm—Hammond & Littell, Weissenberger and Muserlian

[57] ABSTRACT

Novel antidepressant, antiemetic and neuroleptic compositions containing as the active ingredient at least one compound of the formula

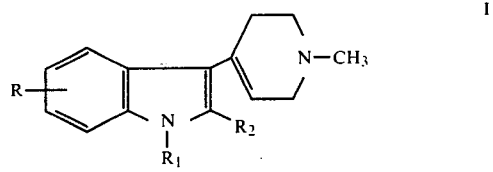

wherein R is selected from the group consisting of hydrogen and methoxy, $R_1$ and $R_2$ are individually selected from the group consisting of hydrogen and methyl and their non-toxic, pharmaceutically acceptable acid addition salts and a novel method of treating psychic disorders in warm-blooded animals.

4 Claims, No Drawings

TREATING PSYCHIC DISORDERS WITH TETRAHYDROPYRIDIN-4-YL-1H-INDOLES

STATE OF THE ART

Various related indoles are described in U.S. Pat. No. 3,993,764, French Pat. No. 2,227,873, Belgium Pat. No. 858,101 and J. Org. Chem., Vol. 40 17 (1975), p. 2527.

OBJECTS OF THE INVENTION

It is an object of the invention to provide the novel therapeutic compositions containing as the active ingredient a compound of formula I and their non-toxic, pharmaceutically acceptable acid addition salts.

It is another object of the invention to provide a novel method of treating psychic disorders in warm-blooded animals.

These and other objects and advantages of the invention will become obvious from the following detailed description.

THE INVENTION

The novel compositions for the treatment of psychic disorders of the invention are comprised of an amount of at least one compound of the formula

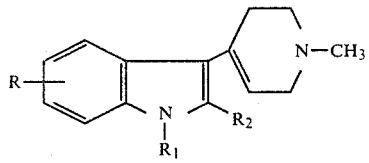

wherein R is selected from the group consisting of hydrogen and methoxy and $R_1$ and $R_2$ are individually selected from the group consisting of hydrogen and methyl and their non-toxic, pharmaceutically acceptable acid addition salts sufficient to treat psychic disorders.

Examples of suitable acids for the non-toxic, pharmaceutically acceptable acid addition salts are mineral acids such as hydrochloric acid, hydrobromic acid, hydroiodic acid, nitric acid, sulfuric acid and phosphoric acid and organic acids such as formic acid, acetic acid, benzoic acid, maleic acid, fumaric acid, succinic acid, tartaric acid, citric acid, glyoxylic acid, oxalic acid, aspartic acid, alkane sulfonic acids such as methane sulfonic acid and arylsulfonic acids such as benzene sulfonic acid.

Among the preferred compounds of formula I are those wherein $R_1$ and $R_2$ are hydrogen and their non-toxic, pharmaceutically acceptable acid addition salts.

Specific preferred compounds are 5-methoxy-3-(1-methyl-1,2,3,6-tetrahydropyridin-4-yl)-1H-indole and 3-(1-methyl-1,2,3,6-tetrahydropyridin-4-yl)-1H-indole, and their non-toxic, pharmaceutically acceptable acid addition salts.

The novel compositions of the invention having antidepressive, antiemetic and neuroleptic activity are comprised of an effective amount of at least one compound of formula I and its non-toxic, pharmaceutically acceptable acid addition salts and an inert pharmaceutical carrier. The compositions may be in the form of tablets, dragees, gelules, granules, capsules, suppositories or injectable solutions or suspensions.

Examples of suitable carriers or excipients are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispersants and emulsifiers.

The compositions are useful for the treatment of psychic troubles, behavior problems, character problems as well as in the treatment of vomiting and nausea of all origins.

Particularly preferred compositions containing compounds of formula I are those wherein $R_1$ and $R_2$ are hydrogen and their non-toxic, pharmaceutically acceptable acid addition salts.

The novel method of the invention for the treatment of psychic disorders in warm-blooded animals, including humans, comprises administering to warm-blooded animals an amount of at least one compound of formula I and its non-toxic, pharmaceutically acceptable acid addition salts sufficient to relieve psychic disorders. The compounds may be administered orally, rectally or parenterally, preferably orally. The usual useful dose is 0,1 to 4 mg/kg when administered orally.

The compounds of formula I may be prepared by the process of J. Org. Chem., Vol. 40 No. 17 (1975), p. 2525 to 2529 and the acid addition salts may be prepared by reacting substantially stoichiometric amounts of the acid and the compound of formula I.

In the following examples there are described several preferred embodiments to illustrate the invention. However, it should be understood that the invention is not intended to be limited to the specific embodiments.

EXAMPLE 1

Acid succinate of 5-methoxy-3-(1-methyl-1,2,3,6-tetrahydropyridin-4-yl)-1H-indole Using the procedure of J. Org. Chem., Vol. 40, No. 17 (1975), p. 2525, 1-methyl-piperidone and 5-methoxy-1H-indole were condensed in refluxing acetic acid in the presence of phosphoric acid to obtain 5-methoxy-3-(1-methyl-1,2,3,6-tetrahydropyridin-4-yl)-1H-indole melting at 235° C.

3.5 g of the said product were dissolved in a solution of 1.7 g of succinic acid in 25 ml of methanol and the mixture was stirred for 30 minutes at room temperature and then for 2 hours in an ice bath. The mixture was filtered and the product was rinsed with methanol and dried at 50° C. under reduced pressure to obtain 4.17 g of the acid succinate of the said indole melting at 153° C.

Analysis: $C_{19}H_{24}N_2O_5$; molecular weight=360.418.
Calculated: %C 63.32, %H 6.71, %N 7.77. Found: 63.3, 6.9, 7.7.

EXAMPLE 2

3-(1-methyl-1,2,3,6-tetrahydropyridin-4-yl)-1H-indole hydrochloride

Using the same procedure of Example 1, 1-methyl-piperidone and 1H-indole were condensed in refluxing acetic acid in the presence of phosphoric acid to obtain 3-(1-methyl-1,2,3,6-tetrahydropyridin-4-yl)-1H-indole melting at 228°~229° C.

A suspension of 4.12 g of the said product in 80 ml of iced ethanol was adjusted with stirring to a pH of 1 by addition of an ethanol solution of gaseous hydrogen chloride and the mixture was stirred for one hour at 0° C. and was filtered. The recovered product was rinsed with ethanol and the 4.6 g of raw product was dissolved in 100 ml of refluxing methanol. The solution was filtered hot and crystallization was induced. The mixture was iced for 2 hours and was filtered. The product was rinsed with methanol to obtain 3.04 g of the hydrochloride of the said indole melting at 241°–243° C.

Analysis: $C_{14}H_{16}N_2.HCl$; molecular weight = 248.762. Calculated: %C 67.59, %H 6.88, %N 11.26, %Cl 14.25. Found: 67.7, 7.0, 10.9, 14.2.

EXAMPLE 3

Tablets were prepared containing 25 mg of the product of Example 1 and sufficient excipient of lactose, starch, talc and magnesium stearate for a final weight of 200 mg. Injectable solutions were prepared with 25 mg of the compound of Example 2 and sufficient sterile water for a final volume of 2 ml.

PHARMACOLOGICAL DATA

A. Potentialization of amphetamine stereotypies

The tests were effected on groups of 5 male rats weighing 150 to 180 g with the animals individually placed in a grilled cage (29×25×17 cm) containing a few scraps of wood chips. A delay of one hour was observed between the intraperitoneal administration of the test compound and the intraperitoneal injection of 5 mg/kg of dexamphetamine sulfate and the behavior of the animals were noted every half hour for 5 hours with the preconceived readings of Halliwell et al [Brit. J. Pharmacol., Vol. 23 (1964), p. 330–350] as follows: The animal was asleep (0), the animal was awake but immobile (1), the animal was turning in the cage (2), the animal was sniffing the cover (3), the animal was licking the sides (4), the animal was touching the scraps of wood chips or bars of the cage with his teeth (5), and the animal was gnawing on the bars of the cage or the scraps of wood chips (6).

The intensity of the stereotypies were expressed in the form of a score of 0 to 30 corresponding to the total of the values obtained for each group of 5 rats. The sum of the scores totaled in 5 hours was calculated. The dose of the test compound which augmented by about 100% the sum of the scores in 5 hours was 2 mg/kg for the product of Example 1 and 20 mg/kg for the product of Example 2.

B. Antagonism to apomorphine stereotypies

The test was inspired by Janssen et al/Arzneim. Forsch. Vol. 15 (1965), p. 104–117; Vol. 17 (1967), p. 841–854/with group of 5 rats with each rat being individually placed in a plexiglass box (20×10×10 cm; Nicolet) with the bottom covered with a thin layer of wood chips. A dose of 1.5 mg/kg of apomorphine hydrochloride was intravenously administered 30 minutes after intraperitoneal administration of the test product. The animals were observed every minute for 15 minutes after the apomorphine injection and the stereotypic movements of the oral sphere were evaluated by the method of Boissier et al/Therapie., Vol. 25, (1970), p. 933–949/as follows: no characteristic reaction (0), a few sniffles, lickings and chewings (1), intense sniffles and continous lickings (2) and continous chewings (3). The intensity of the stereotypies were expressed in a form of a score of 0 to 15 corresponding to the total of the values obtained for each group of 5 rats, 15 minutes after the apomorphine injection. The dose which reduced by 50% the total of the scores was 20 mg/kg for the compound of Example 2.

C. Potentialization of Yohimbine toxicity

The test used was that of Quinton [Brit. J. Pharmacol., Vol. 21 (1963) p. 51] in which a sublethal dose of 30 mg/kg of yohimbine hydrochloride was intraperitoneally injected to groups of 10 male mice weighing 22 to 24 g. The test compound was intraperitoneally administered 1 hour before the yohimbine injection and the number of dead mice was determined 24 hours after the yohimbine injection. The product of Example 2 potentialized the toxicity of the yohimbine at a dose of 35 mg/kg while the product of Example 1 did so at a dose of 10 mg/kg.

D. Antagonism towards catalepsy caused by prochlorpemazine

The test was effected on groups of 5 male rats weighing about 100 g and the test compound was administered intraperitoneally simultaneously with the intraperitoneal administration of 15 mg/kg of prochlorpemazine. The catalepsy was observed every hour for 7 hours following the test of crossing of homolateral paws [Boissier et al., Therapie, Vol. 18 (1963), p. 1257–1277] with the following notations: The animal refused to cross the front paws with the homolateral rear paws (0), the animal accepted the crossing only for one side (0.5) and the animal accepted the crossing of both sides (1). The compound of Example 2 opposed catalepsy induced by prochlorpemazine at a dose of 20 mg/kg.

E. Antiemetic activity

The antagonism to vomitting provoked by apomorphine was studied in dogs [Chen et al., J. Pharmac. Exp. Therap., Vol. 93 (1959), p. 245–250] and the number of vomits provoked by subcutaneous injection of 0.1 mg/kg of apomorphine hydrochloride was determined for each animal 8 days before the test. The test compound in aqueous solution was subcutaneously administered at varying doses one half hour before the apomorphine hydrochloride. The compound of Example 1 was antagonistic to the provoked vomits by reducing the same by 50% at 0.08 mg/kg and the compound of Example 2 was effective at 0.05 mg/kg.

F. Acute toxicity

The acute toxicity was determined on groups of 10 mice weighing about 20 g and the test compounds were intraperitoneally administered at increasing doses. The mortality was determined 48 hours after the administration and the $LD_{50}$ dose for the compounds of Examples 1 and 2 was 150 and 120 mg/kg, respectively.

Various modifications of the products and processes of the invention may be made without departing from the spirit or scope thereof and it is to be understood that the invention is intended to be limited only as defined in the appended claims.

We claim:

1. A method of treating psychic disorders in warm-blooded animals comprising administering to warm-blooded animals an amount of at least one compound of the formula

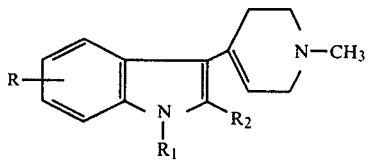

wherein R is selected from the group consisting of hydrogen and methoxy, $R_1$ and $R_2$ are individually selected from the group consisting of hydrogen and methyl and their non-toxic, pharmaceutically acceptable acid addition salts sufficient to relieve psychic disorders.

2. A method of claim 1 wherein $R_1$ and $R_2$ are hydrogen.

3. A method of claim 1 wherein the active ingredient is selected from the group consisting of 5-methoxy 3-(1-methyl-1,2,3,6-tetrahydropyridin-4-yl)-1H-indole and its non-toxic, pharmaceutically acceptable acid addition salts.

4. A method of claim 1 wherein the active ingredient is selected from the group consisting of 3-(1-methyl-1,2,3,6-tetrahydropyridin-4-yl)-1H-indole and its non-toxic, pharmaceutically acceptable acid addition salts.

* * * * *